(12) United States Patent
Tang et al.

(10) Patent No.: US 9,203,259 B2
(45) Date of Patent: Dec. 1, 2015

(54) SENSING DEVICE, SENSING CHARGER AND SENSING EMERGENCY LAMP

(75) Inventors: Guangshi Tang, Dongguan (CN); Shaoming Yu, Dongguan (CN)

(73) Assignee: JIE DU ELECTRONICS TECHNOLOGY CO., LTD., Dongguan, Guangdong Province (CN)

( * ) Notice: Subject to any disclaimer, the term of this patent is extended or adjusted under 35 U.S.C. 154(b) by 323 days.

(21) Appl. No.: 14/000,491

(22) PCT Filed: Feb. 25, 2012

(86) PCT No.: PCT/CN2012/071640
§ 371 (c)(1),
(2), (4) Date: Aug. 20, 2013

(87) PCT Pub. No.: WO2013/097338
PCT Pub. Date: Jul. 4, 2013

(65) Prior Publication Data
US 2013/0320873 A1  Dec. 5, 2013

(30) Foreign Application Priority Data
Dec. 31, 2011  (CN) ...................... 2011 2 0575122 U

(51) Int. Cl.
| | |
|---|---|
| *H05B 37/00* | (2006.01) |
| *H02J 7/02* | (2006.01) |
| *G01N 27/72* | (2006.01) |
| *H05B 37/02* | (2006.01) |
| *H01F 38/14* | (2006.01) |
| *H02J 5/00* | (2006.01) |

(52) U.S. Cl.
CPC ................ *H02J 7/025* (2013.01); *G01N 27/72* (2013.01); *H01F 38/14* (2013.01); *H02J 5/005* (2013.01); *H05B 37/0227* (2013.01)

(58) Field of Classification Search
CPC ...... H05B 37/0027; H02J 5/005; H02J 7/025; H01F 38/14
See application file for complete search history.

(56) References Cited

U.S. PATENT DOCUMENTS 5,680,016 A * 10/1997 Valcke .................. H05B 41/16
315/176
5,939,832 A * 8/1999 Franck ............... H05B 41/2985
315/119

* cited by examiner

*Primary Examiner* — Hai L Nguyen
(74) *Attorney, Agent, or Firm* — Shimokaji IP

(57) ABSTRACT

A sensing device includes a sensing transmitting module and a sensing receiving module respectively mounted in a first housing and a second housing. And an output terminal of the sensing transmitting module and an input terminal of the sensing receiving module are provided with a sensing coil and an electromagnetic rod respectively, the first housing and the second housings are cooperated with each other, and the electromagnetic rod is inserted into the sensing coil, so that the sensing coil or the electromagnetic rod is placed in magnetic field generated by the electromagnetic rod or the sensing coil thereby generating sensing voltage. The sensing parts are formed of the sensing coil and the electromagnetic rod, which significantly reduces the amount of the copper wires in the sensing coil and the electromagnetic rod, therefore the sensing device has a smaller size, lighter weight and lower cost.

13 Claims, 9 Drawing Sheets

SENSING DEVICE, SENSING CHARGER AND SENSING EMERGENCY LAMP

RELATED APPLICATIONS

This application claims the benefit of priority to Chinese Patent Application No. 201120575122.5, filed Dec. 31, 2011, with a title of "SENSING DEVICE, SENSING CHARGER AND SENSING EMERGENCY LAMP", which is hereby incorporated by reference in its entirety.

FIELD OF THE INVENTION

The present invention relates to a sensing device, and more particularly to a sensing device with small size and lower cost, a sensing charger and a sensing emergency lamp with the same.

BACKGROUND OF THE INVENTION

With improvement of people's living standard, electronic products (such as flashlight, electric fan, electric shaver, desk lamp, headlight, camping light) have become necessary supplies. These electronic products are needed to charge up frequently due to the frequent use and the limitation of using places. Conventional charging includes two ways, one way is connecting the electronic product with the charging plug via a data line, and therefore electricity can be conducted into the battery so as to store the electricity into the battery; the other way is disassembling the battery from the electronic product and assembling it to the charger to charge. One on hand, since the first way must use data line to accomplish the charging, one end of the data line must be inserted into the electronic product while charging and then pulled out after charging, which is quite inconvenient and problems such as disconnection or socket looseness etc. will be generated. Thus the charging effect is unstable and furthermore it will damage the electronic products. On the other hand, regarding to the emergency lamp and camping light etc., as these electronic products are often in the state of charge when they are unused, and when they are needed to use, it's hard for user to take the product from the charge base in time. Therefore, non-contact charging equipments have been developed.

Referring to US Pub. No. 2010/0066251, which discloses a charging equipment used in the emergency lamp. The charging equipment includes a charger base, a sensing transmitting module mounted in the charger base and a sensing receiving module mounted in a housing of the emergency lamp. Therein, a large sensing coil in the output terminal of the sensing transmitting module encircles a small sensing coil in the input terminal of the sensing receiving module. When operates, electricity inputted from the plug is translated into magnetic energy by the large sensing coil and then the magnetic energy is translated into sensing voltage by the small sensing coil so as to charge up the rechargeable battery of the emergency lamp. However, as the sensing parts of the above-mentioned charging equipment are formed by a small sensing coil and a large sensing coil encircled the small sensing coil, thus the total sensing coils are too large, the copper wires needed to use are increased, therefore the weight is increased which causes a high cost. Moreover, as the size of the sensing parts is overlarge, thus it's not applicable to small products.

Thus, there is a need for a sensing charger to overcome the above-mentioned drawbacks.

SUMMARY OF THE INVENTION

One objective of the present invention is to provide a small sensing device with small size, light weight and lower cost.

Another objective of the present invention is to provide a small sensing charger with small size, light weight and lower cost.

Still an objective of the present invention is to a small sensing emergency lamp with small size, light weight and lower cost.

To achieve the above-mentioned objectives, the present invention provides a sensing device which is used for supplying power for or charging up electronic products such as flashlight, electric fan, electric shaver, desk lamp, headlight, camping light etc. The sensing device includes a sensing transmitting module and a sensing receiving respectively module which are mounted in a first housing and a second housing separated from each other. Therein, an output terminal of the sensing transmitting module and an input terminal of the sensing receiving module are respectively provided with a sensing coil and an electromagnetic rod corresponding to each other, the first housing and the second housing are cooperated with each other in a concavo-convex manner, and the electromagnetic rod is inserted into the sensing coil, so that the sensing coil or the electromagnetic rod of the sensing receiving module is placed in magnetic field generated by the electromagnetic rod or the sensing coil, thereby generating sensing voltage. Therein, when the sensing transmitting module is mounted in the first housing, the sensing receiving module is mounted in the second housing, and vice versa. When the sensing coil is formed on the output terminal of the sensing transmitting module, the electromagnetic rod is formed on the input terminal of the sensing receiving module, and vice versa.

Preferably, the sensing transmitting module and the sensing receiving module include a first sensing circuit and a second sensing circuit cooperated with each other, and the second sensing circuit is a resonant sensing circuit whose inductance is formed of the sensing coil or electromagnetic rod. Based on the design, the receiving way by using resonant sensing can improve the receiving effect of the sensing receiving module.

Preferably, the sensing transmitting module has an output frequency in a range of 250 KHZ~400 KHZ. Compared with the output frequency 150 KHZ of the conventional, the present invention have increased that to 250 KHZ~400 KHZ which is significantly improved the sensing effect between the sensing coil and the electromagnetic rod.

Preferably, the sensing transmitting module includes a voltage dropping circuit connecting with a power source, a first rectification filter circuit connecting with an output terminal of the voltage dropping circuit, an electromagnetic oscillation circuit connecting with an output terminal of the first rectification filter circuit, and a first sensing circuit connecting with an output terminal of the electromagnetic oscillation circuit. The sensing receiving module includes a second sensing circuit cooperating with the first sensing circuit and generating sensing voltage, a second rectification filter circuit connecting with the second sensing circuit, and a voltage regulator circuit connecting with the second rectification filter circuit, and an output terminal of the voltage regulator circuit is connected with and supplying power for a load. Based on this design, the present invention can supply stable power source for a load with non-contact way.

As a first preferable embodiment, a recess is formed on the first housing, and a protective rod is protruded from the bottom of the recess, and the protective rod is hollowed in which the electromagnetic rod is mounted; a ringed protective sleeve is formed on the second housing and cooperated with the recess having the protective rod in a concavo-convex manner, whose ring center is encircling the protective rod and whose ring body is hollowed, and the sensing coil is mounted in the protective sleeve and encompassing the ring center.

As a second preferable embodiment, a ringed protective sleeve whose ring body is hollowed is formed on the first housing, and the sensing coil is mounted within the protective sleeve and encompassing a ring center thereof; a protective rod which is available to extend to the ring center of the protective rod and cooperate with the protective sleeve is formed on the second housing, and the protective rod is hollowed in which the electromagnetic rod is mounted.

As a third preferable embodiment, a protective rod is protruded on the first housing, and the protective rod is hollowed in which the electromagnetic rod is mounted; a recess cooperating with the protective rod is formed on the second housing by recessing inward, and the sensing coil is mounted in the second housing and encompassing the recess.

In comparison with the prior art, the sensing parts of the sensing device of the present invention includes the sensing coils and the electromagnetic rod cooperated with each other, and the electromagnetic rod is inserted into the sensing coils, which significantly reduces the size of the copper wires in the sensing coils and the electromagnetic rod. Due to the copper wires are reduced, thus the sensing charger and the sensing emergency lamp can possess a smaller size, lighter weight and lower cost.

Accordingly, the present invention provides a sensing charger for charging electronic equipments (such as flashlight, electric fan, electric shaver, desk lamp, headlight, camping light etc.) The sensing charger includes a charger base including a power source input interface; and a sensing device including a sensing transmitting module and a sensing receiving module which are respectively mounted in a first housing and a second housing separated from each other. And the sensing transmitting module is mounted in a housing of the charger base and connected with the power source input interface, and the sensing receiving module is mounted within a housing of the electronic equipment and connected with rechargeable battery of the electronic equipment. Concretely, an output terminal of the sensing transmitting module and an input terminal of the sensing receiving module are respectively provided with a sensing coil and a electromagnetic rod corresponding to each other, the first housing and the second housing are cooperated with each other in a concavo-convex manner so that the electromagnetic rod is inserted into the sensing coil, and the sensing coil or the electromagnetic rod of the sensing receiving module is placed in magnetic field generated by the electromagnetic rod or the sensing coil, thereby generating sensing voltage. Therein, the sensing transmitting module is arranged for translating external power supply into magnetic energy, and the sensing receiving module is arranged for generating sensing voltage according to the magnetic energy so as to charge up the rechargeable battery. Concretely, the power source input interface can be the power source plug formed on the charger base, or other interfaces such USB etc. And the first housing and the second housing are formed by a housing of the charger base and a housing of the electronic equipment.

Preferably, the sensing transmitting module and the sensing receiving module include a first sensing circuit and a second sensing circuit cooperated with each other, and the second sensing circuit is a resonant sensing circuit whose inductance is formed of the sensing coil or electromagnetic rod. Based on the design, the receiving way by using resonant sensing can improve the receiving effect of the sensing receiving module.

Preferably, the sensing transmitting module has an output frequency in a range of 250 KHZ~400 KHZ. Compared with the output frequency 150 KHZ of the conventional, the present invention have increased that to 250 KHZ~400 KHZ which is significantly improved the sensing effect between the sensing coil and the electromagnetic rod.

Preferably, the sensing transmitting module includes a voltage dropping circuit connecting with a power source, a first rectification filter circuit connecting with an output terminal of the voltage dropping circuit, an electromagnetic oscillation circuit connecting with an output terminal of the first rectification filter circuit, and a first sensing circuit connecting with an output terminal of the electromagnetic oscillation circuit. The sensing receiving module includes a second sensing circuit cooperating with the first sensing circuit and generating sensing voltage, a second rectification filter circuit connecting with the second sensing circuit, and a voltage regulator circuit connecting with the second rectification filter circuit, and an output terminal of the voltage regulator circuit is connected with the rechargeable battery.

As a first preferable embodiment, a recess is formed on the first housing, and a protective rod is protruded from the bottom of the recess, and the protective rod is hollowed in which the electromagnetic rod is mounted; a ringed protective sleeve is formed on the second housing and cooperated with the recess having the protective rod, whose ring center is encircling the protective rod and whose ring body is hollowed, and the sensing coil is mounted in the protective sleeve and encompassing the ring center. Concretely, the protective rod is formed on the center of the recess, and the recess can be formed on the housing of the electronic product, and the ringed protective sleeve can be formed on the housing of the charger base accordingly.

As a second preferable embodiment, a ringed protective sleeve whose ring body is hollowed is formed on the first housing, and the sensing coil is mounted in the protective sleeve and encompassing a ring center thereof; a protective rod which is available to extend to the ring center of the protective rod and cooperate with the protective sleeve is formed on the second housing, and the protective rod is hollowed in which the electromagnetic rod is mounted. Concretely, the ringed protective sleeve can be formed on the housing of the electronic product, and the protective rod can be formed on the housing of the charger base accordingly.

As a third preferable embodiment, a protective rod is protruded on the first housing, and the protective rod is hollowed in which the electromagnetic rod is mounted; a recess cooperating with the protective rod is formed on the second housing by recessing inward, and the sensing coil is mounted in the second housing and encompassing the recess. Concretely, the protective rod can be formed on the housing of the electronic product, and the recess can be formed on the housing of the charger base accordingly.

In comparison with the prior art, the sensing parts of the sensing charger of the present invention includes the sensing coils and the electromagnetic rod cooperated with each other, and the electromagnetic rod is inserted into the sensing coils, which significantly reduces the size of the copper wires in the sensing coils and the electromagnetic rod. Due to the copper wires are reduced, thus the sensing charger and the sensing emergency lamp can possess a smaller size, lighter weight and lower cost.

Accordingly, the present invention provides a sensing emergency lamp which includes a charger base including a power source input interface, a lighting device including a housing in which rechargeable battery, sensor, lighting control circuit and lighting circuit are mounted, and a sensing device including a sensing transmitting module and a sensing receiving module which are mounted in a separated first housing and a separated second housing respectively. Concretely, the sensing transmitting module is mounted in a housing of the charger base and connected with the power source input interface, the sensing receiving module is mounted in the housing of the lighting device and connected with the rechargeable battery of the lighting device, the rechargeable battery is connected with and supplying power source for the lighting circuit, and the turn-on and turn-off of the lighting circuit is controlled by the lighting control circuit according to a signal sensed by the sensor. Therein, an output terminal of the sensing transmitting module and an input terminal of the sensing receiving module are respectively provided with a sensing coil and a electromagnetic rod corresponding to each other, the first housing and the second housing are cooperated with each other in a concavo-convex manner so that the electromagnetic rod is inserted into the sensing coil, and the sensing coil or the electromagnetic rod of the sensing receiving module is placed in magnetic field generated by the electromagnetic rod or the sensing coil, thereby generating sensing voltage. Concretely, the power source input interface can be the power source plug formed on the charger base, or other interfaces such USB etc. And the first housing and the second housing are formed by a housing of the charger base and a housing of the electronic equipment.

Preferably, the output terminal of the sensing receiving module is connected with the lighting circuit. Based on this design, the sensing device can be used for charging up the rechargeable battery, or supplying power for the lighting circuit.

Preferably, the sensing transmitting module and the sensing receiving module include a first sensing circuit and a second sensing circuit cooperated with each other, and the second sensing circuit is a resonant sensing circuit whose inductance is formed of the sensing coil or electromagnetic rod. Based on the design, the receiving way by using resonant sensing can improve the receiving effect of the sensing receiving module.

Preferably, the sensing transmitting module has an output frequency in a range of 250 KHZ~400 KHZ. Compared with the output frequency 150 KHZ of the conventional, the present invention have increased that to 250 KHZ~400 KHZ which is significantly improved the sensing effect between the sensing coil and the electromagnetic rod.

Preferably, the sensing transmitting module includes a voltage dropping circuit connecting with a power source, a first rectification filter circuit connecting with an output terminal of the voltage dropping circuit, an electromagnetic oscillation circuit connecting with an output terminal of the first rectification filter circuit, and a first sensing circuit connecting with an output terminal of the electromagnetic oscillation circuit. The sensing receiving module includes a second sensing circuit cooperating with the first sensing circuit and generating sensing voltage, a second rectification filter circuit connecting with the second sensing circuit, and a voltage regulator circuit connecting with the second rectification filter circuit, and an output terminal of the voltage regulator circuit is connected with the rechargeable battery.

As a first preferable embodiment, a recess is formed on the first housing, and a protective rod is protruded from the bottom of the recess, and the protective rod is hollowed in which the electromagnetic rod is mounted; a ringed protective sleeve is formed on the second housing and cooperated with the recess having the protective rod, whose ring center is encircling the protective rod and whose ring body is hollowed, and the sensing coil is mounted in the protective sleeve and encompassing the ring center. Concretely, the protective rod is formed on the center of the recess, and the recess can be formed on the housing of the lighting device, and the ringed protective sleeve can be formed on the housing of the charger base accordingly.

As a second preferable embodiment, a ringed protective sleeve whose ring body is hollowed is formed on the first housing, and the sensing coil is mounted in the protective sleeve and encompassing a ring center thereof; a protective rod which is available to extend to the ring center of the protective rod and cooperate with the protective sleeve is formed on the second housing, and the protective rod is hollowed in which the electromagnetic rod is mounted. Concretely, the ringed protective sleeve can be formed on the housing of the lighting device, and the protective rod can be formed on the housing of the charger base accordingly.

As a third preferable embodiment, a protective rod is protruded on the first housing, and the protective rod is hollowed in which the electromagnetic rod is mounted; a recess cooperating with the protective rod is formed on the second housing by recessing inward, and the sensing coil is mounted in the second housing and encompassing the recess. Concretely, the protective rod can be formed on the housing of the lighting device, and the recess can be formed on the housing of the charger base accordingly.

In comparison with the prior art, the sensing parts of the sensing emergency lamp of the present invention includes the sensing coils and the electromagnetic rod cooperated with each other, and the electromagnetic rod is inserted into the sensing coil, which significantly reduces the size of the copper wires in the sensing coils and the electromagnetic rod. Due to the copper wires are reduced, thus the sensing charger and the sensing emergency lamp can possess a smaller size, lighter weight and lower cost.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

For detailedly explaining the technical contents, structures, objectives and effect of the present invention, various preferred embodiments of the invention will now be described with reference to the figures.

Figure 1A:
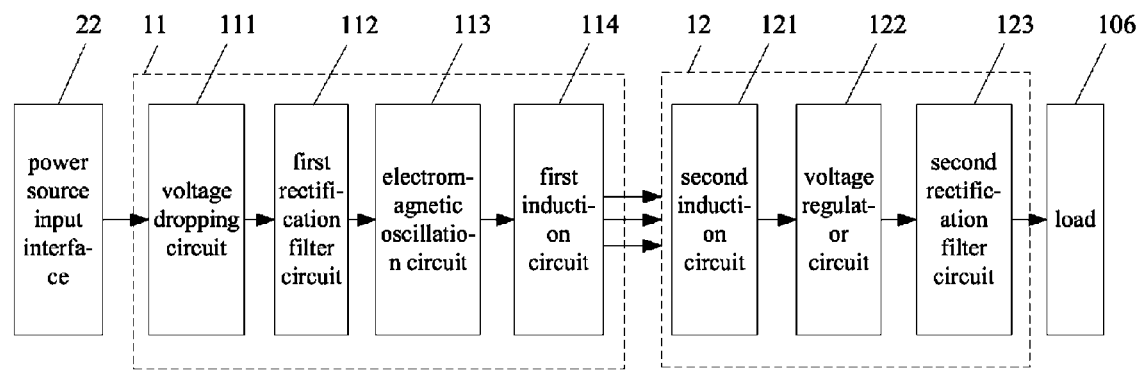
FIG. 1a is a schematic view of a sensing device of the present invention.
Figure 1B:
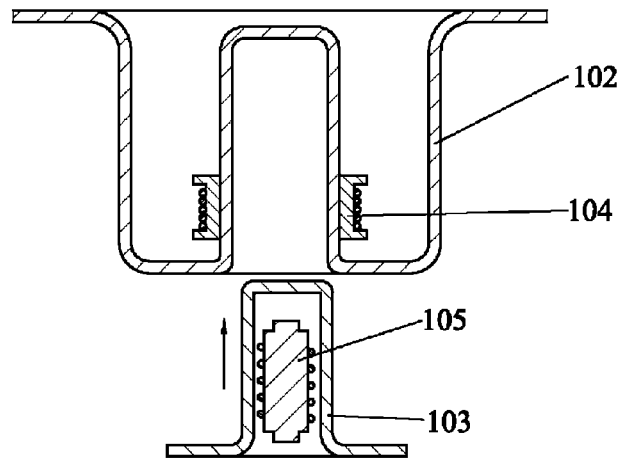
FIG. 1b is a schematic view of sensing parts of the sensing device of the present invention.
Figure 1C:
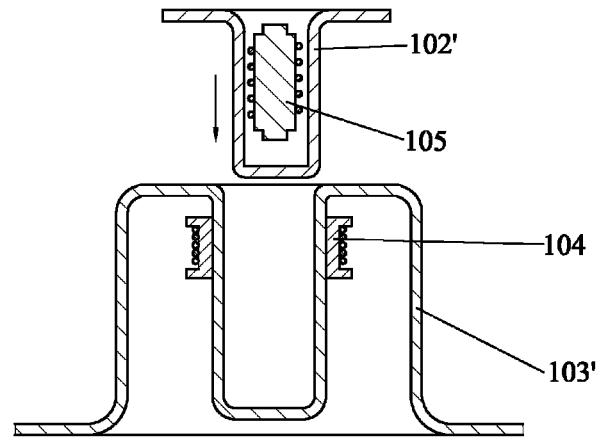
FIG. 1c is another schematic view of a sensing part of the sensing device of the present invention.
Figure 2:
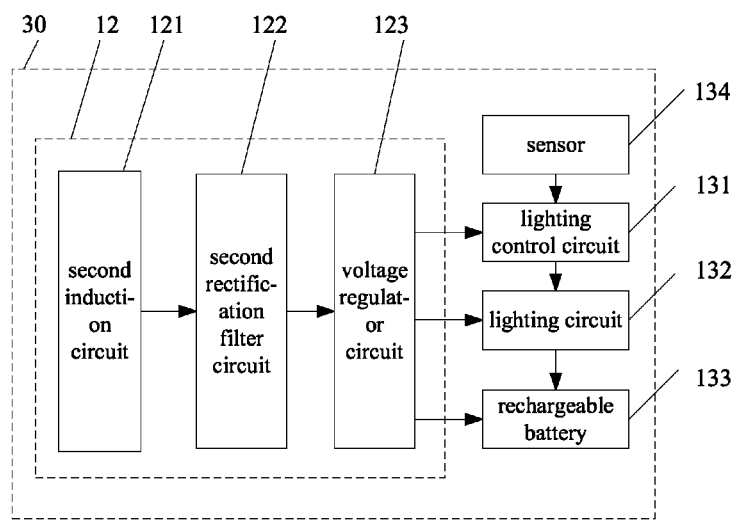
FIG. 2 is a schematic view of a lighting device of the present invention.

Referring to FIGS. 1a-1c, the present invention discloses a sensing device 10 which is used for supplying power for or charging up the electronic products such as flashlight, electric fan, electric shaver, desk lamp, headlight, camping light etc. The sensing device 10 includes a sensing transmitting module 11 mounted in a first housing 102 or 102' and a sensing receiving module 12 mounted in a second housings 103 or 103'. A recess and a protrusion cooperated with each other in a concavo-convex manner are formed on the first housing 102 or 102' and the second housing 103 or 103' respectively. And a sensing coil 104 and a electromagnetic rod 105 corresponding to each other are formed on the output terminal of the sensing transmitting module 11 and the input terminal of the sensing receiving module 12 respectively. When the sensing device 10 is used for charging up or supplying power for the electronic products, the first housing 102 or 102' is equivalent to a housing of a charger base, and the second housing 103 or 103' is equivalent to a housing of the electronic product.

Referring to FIG. 1b, the sensing coil 104 is encircled on the recess of the first housing 102 which forms the output terminal of the sensing transmitting module 11, and the electromagnetic rod 105 is mounted in the protrusion of the second housing 103 which forms the input terminal of the sensing receiving module 12. After the protrusion is extended to the recess to match the first housing 102 with the second housing 103, the electromagnetic rod 105 is inserted into the sensing coil 104 thereby the sensing coil 104 of the sensing receiving module 12 is positioned within the electromagnetic rod 105 of the sensing transmitting module 11 and generated sensing voltage accordingly.

Referring to FIG. 1c, as another embodiment of the present invention, the electromagnetic rod 105 is mounted in the protrusion of the first housing 102' which forms the output terminal of the sensing transmitting module 11, and the sensing coil 104 is encircled on the recess of the second housing 103' which forms the input terminal of the sensing receiving module 12. After the protrusion is extended to the recess to match the first housing 102' with the second housing 103', the electromagnetic rod 105 is inserted into the sensing coil 104 thereby the sensing coil 104 of the sensing receiving module 12 is positioned within the electromagnetic rod 105 of the sensing transmitting module 11 and generated sensing voltage accordingly.

Referring to FIG. 1a again, the sensing transmitting module 11 includes a voltage dropping circuit 111 connecting with an power source input interface 22, a first rectification filter circuit 112 connecting with an output terminal of the voltage dropping circuit 111, an electromagnetic oscillation circuit 113 connecting with an output terminal of the first rectification filter circuit 112, and a first sensing circuit 114 connecting with an output terminal of the electromagnetic oscillation circuit 113. The sensing receiving module 12 includes a second sensing circuit 121 cooperating with the first sensing circuit 114 and generating sensing voltage, a second rectification filter circuit 122 connecting with the second sensing circuit 121, and a voltage regulator circuit 123 connecting with the second rectification filter circuit 122, and an output terminal of the voltage regulator circuit 123 is connected with a load 106.

As a preferred embodiment, the second sensing circuit 121 is a resonant sensing circuit whose inductance is formed of the sensing coil 104 or electromagnetic rod 105. And the sensing transmitting module 11 has an output frequency in a range of 250 KHZ~400 KHZ.

Now turning to FIGS. 2-11, the present invention discloses a sensing emergency lamp 100, which includes a charger base 20 (20a, 20b), a lighting device 30 (30a, 30b) and a sensing device 10. The charger base 20 (20a, 20b) has a power source input interface 22 formed thereon, and the housing 301 of the lighting device 30 (30a, 30b) has rechargeable battery 133, sensor 134, lighting control circuit 131 and lighting circuit 132 mounted therein. The sensing transmitting module 11 of the sensing device 10 is mounted within the housing 201 of the charger base 20 (20a, 20b) and connected with the power source input interface 22, and the sensing receiving module 12 of the sensing device 10 is mounted within the housing 301 of the lighting device 30 and connected with the rechargeable battery 133 which is connected with the lighting circuit 132 for supplying power. And the lighting control circuit 131 is arranged for controlling the turn-on and turn-off of the lighting circuit 132 according to a signal sensed by the sensor 134. The corresponding sensing coil 104 and the electromagnetic rod 105 are formed on the output terminal of the sensing transmitting module 11 and the input terminal of the sensing receiving module 12 respectively, and the housing 201 of the charger base 20 (20a, 20b) and the housing 301 of the lighting device 30 (30a, 30b) is assembled by a concavo-convex way so that the electromagnetic rod 105 is inserted into the sensing coil 104, thereby the sensing coil 104 or the electromagnetic rod 105 of the sensing receiving module 12 is placed in the magnetic field generated by the electromagnetic rod 105 or sensing coil 104 of the sensing transmitting module 11, so as to generate sensing voltage. Therein, when the sensing coil 104 is mounted within the housing 201 of the charger base 20 (20a, 20b), its electromagnetic rod 105 is mounted in the electromagnetic rod 105 of the sensing transmitting module 11, and vice versa.

Figure 3:
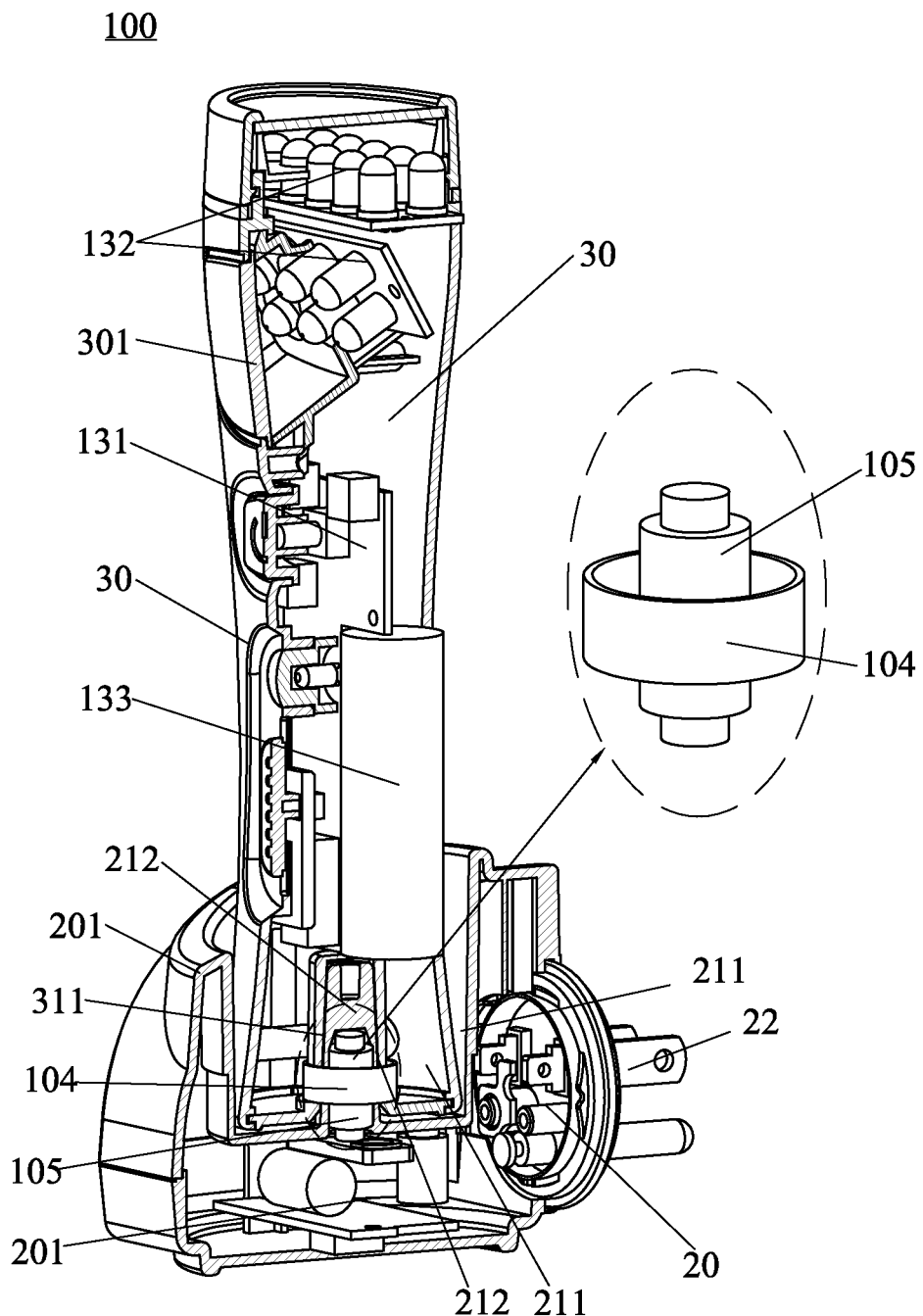
FIG. 3 is a schematic view of a sensing emergency lamp according to a first embodiment of the present invention.
Figure 4:
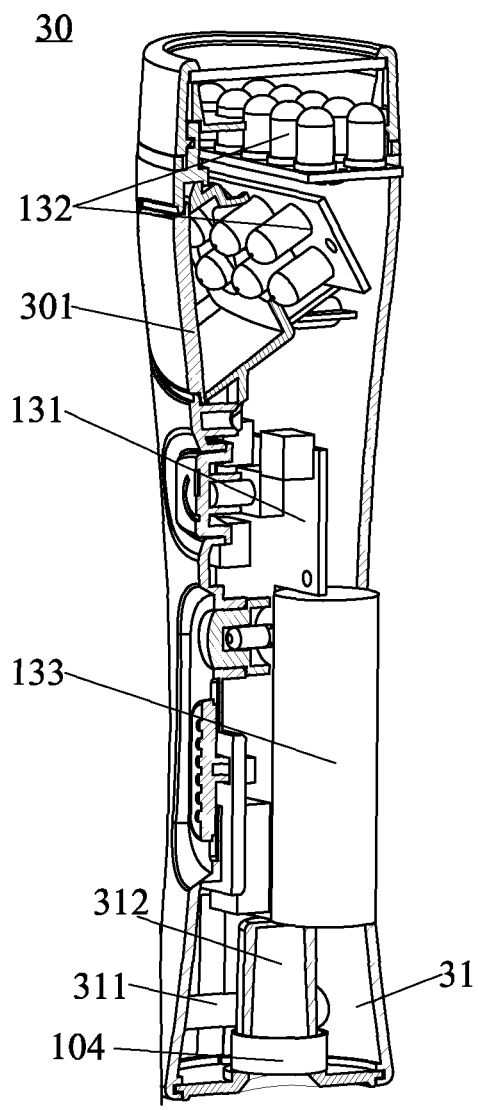
FIG. 4 is a cross-sectional view of the lighting device according to the first embodiment of the present invention.
Figure 5:
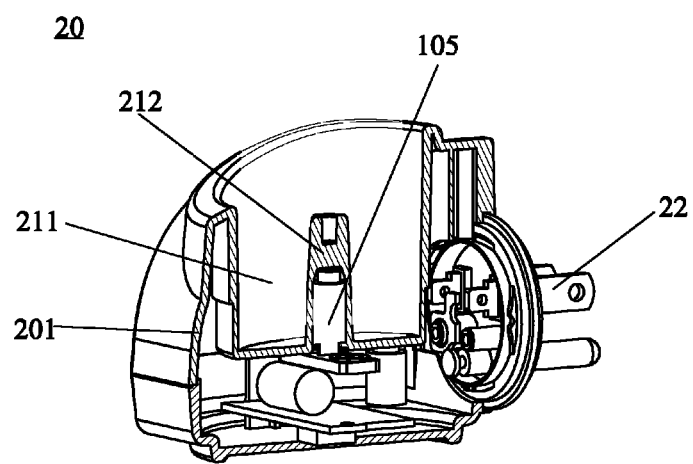
FIG. 5 is a cross-sectional view of a charger base according to the first embodiment of the present invention.

Referring to FIGS. 3-5 which show the sensing emergency lamp 100 according to a first embodiment, a recess 211 is formed on the housing 201 of the charger base 20, and a hollowed protective rod 212 in which the electromagnetic rod 105 is mounted is protruded from the bottom of the recess 211. A ringed protective sleeve 31 is formed on the housing 301 of the lighting device 30 and assembled with the recess 211 of the protective rod 212 via a concavo-convex manner, which includes a ring center 312 encircling the protective rod 212 and a hollowed ring body 311. The sensing coil 104 is mounted in the ring body 311 and encompasses the ring center 312. And the protective rod 212 is formed on the center of the recess 211.

Figure 6:
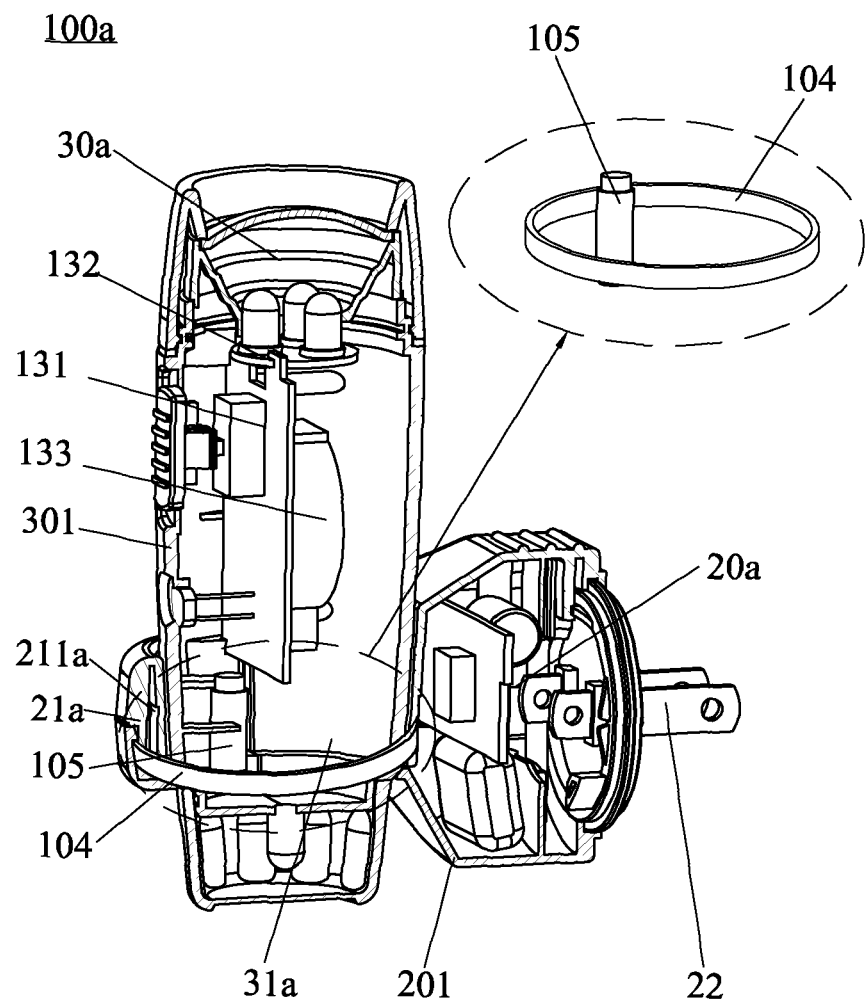
FIG. 6 is a schematic view of a sensing emergency lamp according to a second embodiment of the present invention.
Figure 7:
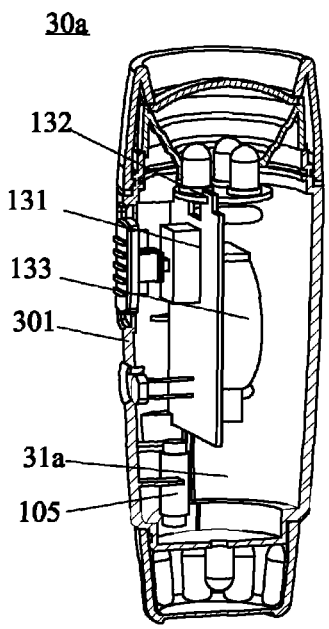
FIG. 7 is a cross-sectional view of the lighting device according to the second embodiment of the present invention.
Figure 8:
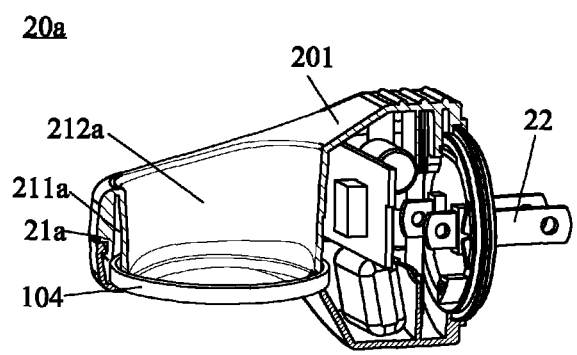
FIG. 8 is a cross-sectional view of a charger base according to the second embodiment of the present invention.

Referring to FIGS. 6-8 which show the sensing emergency lamp 100 according to second embodiment, a protective sleeve 21a including a hollowed ring body 211a and a ring center 212a is formed on the housing 201 of the charger base 20a, and the sensing coil 104 is mounted in the ring body 211a and encompasses the ring center 212a. A protective rod 31a which is available to extend to the ring center 212a and cooperated with the protective sleeve 21a is formed on the housing 301 of the lighting device 30a, and the protective rod 31a is hollowed and in which the electromagnetic rod 105 is mounted.

Figure 9:
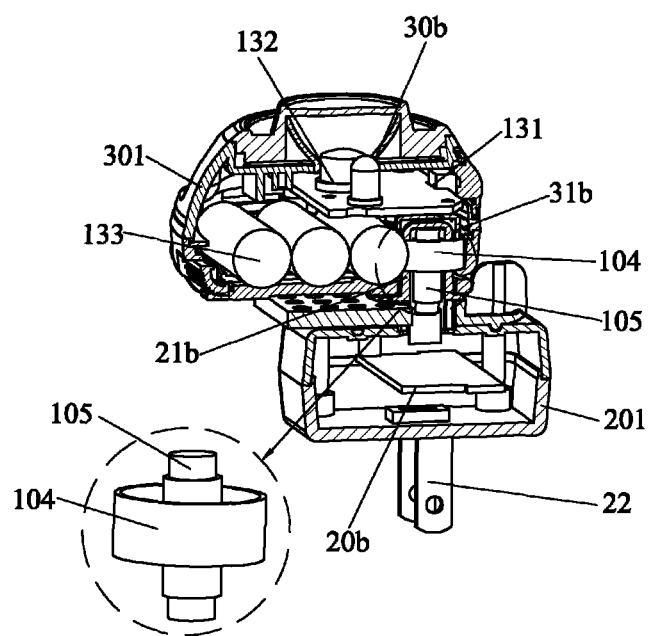
FIG. 9 is a schematic view of a sensing emergency lamp according to a third embodiment of the present invention.
Figure 10:
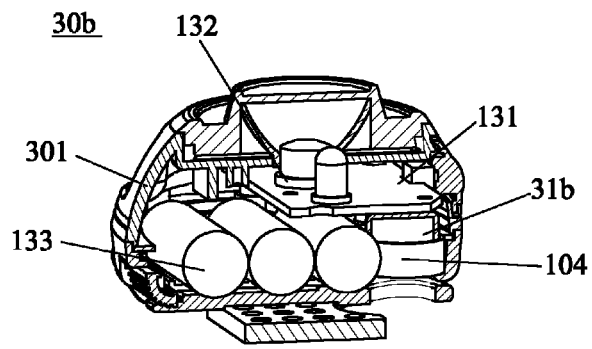
FIG. 10 is a cross-sectional view of the lighting device according to the third embodiment of the present invention.
Figure 11:
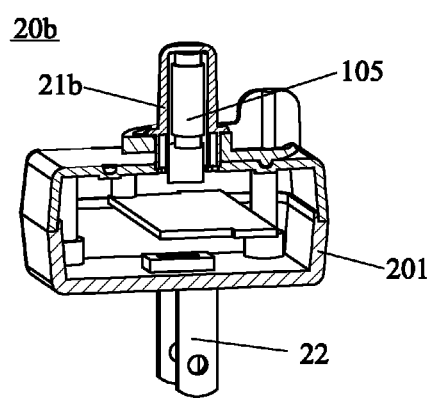
FIG. 11 is a cross-sectional view of a charger base according to the third embodiment of the present invention.

Referring to FIGS. 9-11 which show the sensing emergency lamp 100 according to third embodiment, a protective rod 21b is formed on the housing 201 of the charger base 20b, and the protective rod 21b is hollowed and in which the electromagnetic rod 105 is mounted. A recess 31b is formed on the hollowed housing 301 of the lighting device 30*b* by recessing inward and cooperated with the protective rod 21*b*, and the sensing coil 104 is mounted in the housing 301 and encircles the recess 31*b*.

Moreover, the present invention further discloses a sensing charger applicable to charge up rechargeable battery 133 of the sensing emergency lamp 100. Referring to FIGS. 2-11, the sensing charger includes a charger base 20 (20*a*, 20*b*) and a sensing device 10. The charger base 20 (20*a*, 20*b*) has a power source input interface 22, the sensing transmitting module 11 of the sensing device 10 is mounted in the housing 201 of the charger base 20 (20*a*, 20*b*) and connected with the power source input interface 22, and the sensing receiving module 12 is mounted in the housing 301 of the lighting device 30 (30*a*, 30*b*) and connected with the rechargeable battery 133. Of course, the sensing charger mentioned above is also applicable to charge up the electronic products such as flashlight, electric fan, electric shaver, desk lamp, headlight, camping light etc.

In conclusion, the present invention discloses the sensing device 10, the sensing charger and the sensing emergency lamp 100 with the same, on one hand, the sensing parts of the present invention includes the sensing coil 104 and the electromagnetic rod 105 cooperated with each other, which significantly reduces the size of the copper wires in the sensing coils 104 and the electromagnetic rod 105. Due to the copper wires are reduced, thus the sensing charger and the sensing emergency lamp 100 possess a smaller size, lighter weight and lower cost. On the other hand, as the oscillation frequency of the sensing parts of the sensing device 10 is increased, thus the sensing effect is improved. Furthermore, the present invention applies a receiving way of resonant sensing, which improves the receiving effect of the sensing receiving module 12 thereby decreasing unnecessary wastage.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A sensing device, comprising a sensing transmitting module and a sensing receiving module which are respectively mounted in a first housing and a second housing separated from each other, wherein an output terminal of the sensing transmitting module and an input terminal of the sensing receiving module are respectively provided with a sensing coil and an electromagnetic rod corresponding to each other, the first housing and the second housing are cooperated with each other in a concavo-convex manner, and the electromagnetic rod is inserted into the sensing coil, so that the sensing coil or the electromagnetic rod of the sensing receiving module is placed in magnetic field generated by the electromagnetic rod or the sensing coil of the sensing transmitting module, thereby generating sensing voltage; wherein a ringed protective sleeve whose ring body is hollowed and formed on the first housing, and the sensing coil is mounted within the protective sleeve and encompassing a ring center thereof; a protective rod which is available to extend to the ring center of the protective rod and cooperate with the protective sleeve is formed on the second housing, and the protective rod is hollowed in which the electromagnetic rod is mounted.

2. The sensing device as claimed in claim 1, wherein the sensing transmitting module and the sensing receiving module comprise a first sensing circuit and a second sensing circuit cooperated with each other, and the second sensing circuit is a resonant sensing circuit whose inductance is formed of the sensing coil or electromagnetic rod.

3. The sensing device as claimed in claim 1, wherein the sensing transmitting module has an output frequency in a range of 250 KHZ~400 KHZ.

4. The sensing device as claimed in claim 1, wherein the sensing transmitting module comprises a voltage dropping circuit connecting with a power source, a first rectification filter circuit connecting with an output terminal of the voltage dropping circuit, an electromagnetic oscillation circuit connecting with an output terminal of the first rectification filter circuit, and a first sensing circuit connecting with an output terminal of the electromagnetic oscillation circuit; the sensing receiving module comprises a second sensing circuit cooperating with the first sensing circuit and generating sensing voltage, a second rectification filter circuit connecting with the second sensing circuit, and a voltage regulator circuit connecting with the second rectification filter circuit, and an output terminal of the voltage regulator circuit is connected with and supplying power for a load.

5. A sensing charger, for charging electronic equipments, comprising a charger base having a power source input interface, and a sensing device according to claim 1, wherein the sensing transmitting module is mounted in a housing of the charger base and connected with the power source input interface, and the sensing receiving module is mounted within a housing of the electronic equipment and connected with rechargeable battery of the electronic equipment.

6. The sensing charger as claimed in claim 5, wherein the sensing transmitting module and the sensing receiving module comprise a first sensing circuit and a second sensing circuit cooperated with each other, and the second sensing circuit is a resonant sensing circuit whose inductance is formed of the sensing coil or electromagnetic rod.

7. The sensing charger as claimed in claim 5, wherein the sensing transmitting module has an output frequency in a range of 250 KHZ~400 KHZ.

8. The sensing charger as claimed in claim 5, wherein the sensing transmitting module comprises a voltage dropping circuit connecting with a power source, a first rectification filter circuit connecting with an output terminal of the voltage dropping circuit, an electromagnetic oscillation circuit connecting with an output terminal of the first rectification filter circuit, and a first sensing circuit connecting with an output terminal of the electromagnetic oscillation circuit; the sensing receiving module comprises a second sensing circuit cooperating with the first sensing circuit and generating sensing voltage, a second rectification filter circuit connecting with the second sensing circuit, and a voltage regulator circuit connecting with the second rectification filter circuit, and an output terminal of the voltage regulator circuit is connected with and supplying power for a load.

9. A sensing emergency lamp, comprising a charger base having a power source input interface, a lighting device having a housing in which rechargeable battery, sensor, lighting control circuit and lighting circuit are mounted, and a sensing device according to claim 1, wherein the sensing transmitting module is mounted in a housing of the charger base and connected with the power source input interface, the sensing receiving module is mounted in the housing of the lighting device and connected with the rechargeable battery of the lighting device, the rechargeable battery is connected with and supplying power source for the lighting circuit, and turn-on and turn-off of the lighting circuit is controlled by the lighting control circuit according to a signal sensed by the sensor.

10. The sensing emergency lamp as claimed in claim 9, wherein the sensing transmitting module and the sensing receiving module comprise a first sensing circuit and a second sensing circuit cooperated with each other, and the second sensing circuit is a resonant sensing circuit whose inductance is formed of the sensing coil or electromagnetic rod.

11. The sensing emergency lamp as claimed in claim 9, wherein the sensing transmitting module has an output frequency in a range of 250 KHZ~400 KHZ.

12. The sensing emergency lamp as claimed in claim 9, wherein the sensing transmitting module comprises a voltage dropping circuit connecting with a power source, a first rectification filter circuit connecting with an output terminal of the voltage dropping circuit, an electromagnetic oscillation circuit connecting with an output terminal of the first rectification filter circuit, and a first sensing circuit connecting with an output terminal of the electromagnetic oscillation circuit; the sensing receiving module comprises a second sensing circuit cooperating with the first sensing circuit and generating sensing voltage, a second rectification filter circuit connecting with the second sensing circuit, and a voltage regulator circuit connecting with the second rectification filter circuit, and an output terminal of the voltage regulator circuit is connected with and supplying power for a load.

13. The sensing emergency lamp as claimed in claim 9, wherein the output terminal of the sensing receiving module is connected with the lighting circuit.

\* \* \* \* \*